United States Patent [19]

Gibbens

[11] Patent Number: 4,726,371

[45] Date of Patent: Feb. 23, 1988

[54] SURGICAL CUTTING INSTRUMENT

[76] Inventor: Everett N. Gibbens, 205 E. Gridley Rd., P.O. Box 957, Gridley, Ill. 61744

[21] Appl. No.: 347,283

[22] Filed: Feb. 9, 1982

[51] Int. Cl.⁴ ............................................. A61F 17/32
[52] U.S. Cl. ........................................ 128/305; 30/232
[58] Field of Search ............... 128/305, 309, 318, 361; 30/231, 232, 298; 7/121; 63/1 R, 15.7

[56] References Cited

U.S. PATENT DOCUMENTS

| 107,016 | 9/1870 | Egge et al. | 30/232 |
| 354,363 | 12/1886 | Titus | 30/232 |
| 2,151,846 | 3/1939 | Greneker | 30/298 |
| 2,704,889 | 3/1955 | Delinanos | 7/121 X |
| 2,707,828 | 5/1955 | Stewart | 30/232 |
| 3,736,770 | 6/1973 | Kelrick | 63/15.7 |

FOREIGN PATENT DOCUMENTS

| 539280 | 2/1956 | Italy | 30/232 |
| 6060 | of 1889 | United Kingdom | 7/121 |
| 584404 | 1/1947 | United Kingdom | 63/15.7 |

Primary Examiner—Edward M. Coven
Attorney, Agent, or Firm—Burns, Doane, Swecker & Mathis

[57] ABSTRACT

A surgical cutting instrument is carried on the small finger of a surgeon's hand to enable cuts to be made while the surgeon holds another instrument in the same hand. The cutting instrument cmprises a sleeve mounted on the surgeon's small finger, and a scissor mounted on the sleeve. The sleeve includes a single stationary blade and a single movable blade, each projecting forwardly of the sleeve. The movable blade is mounted for rotation and includes an actuating arm extending generally laterally of the sleeve and toward the adjacent ring finger of the same hand so as to be actuable to a cutting position relative to the stationary blade by bending of the ring finger.

13 Claims, 8 Drawing Figures

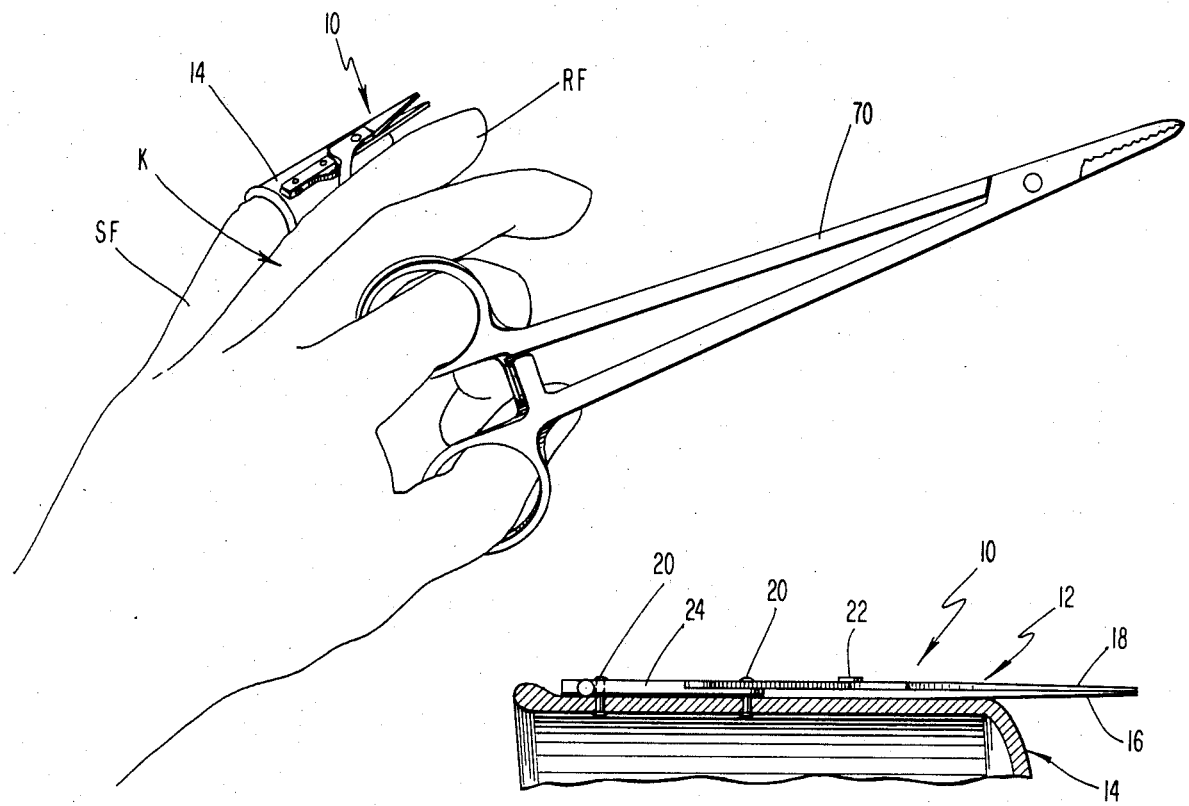
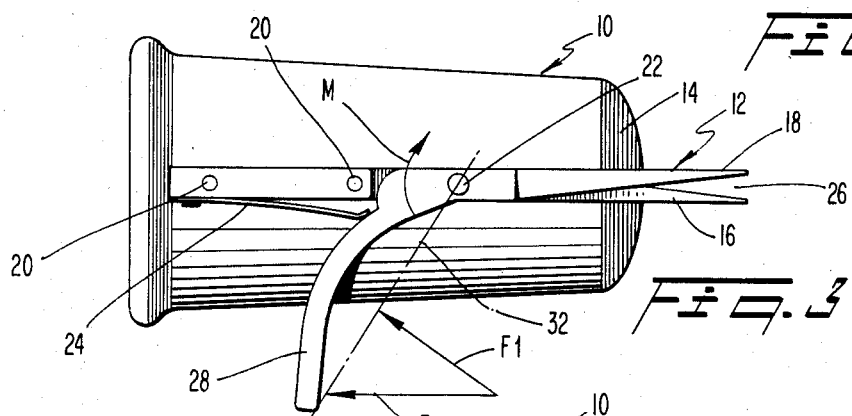
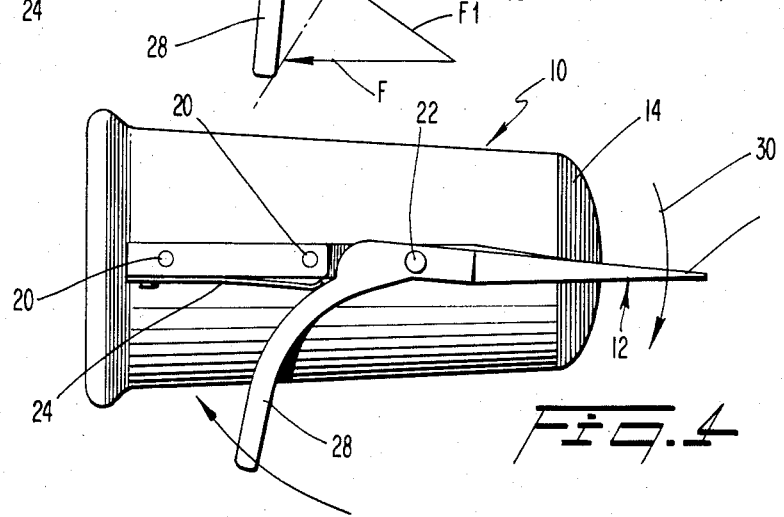

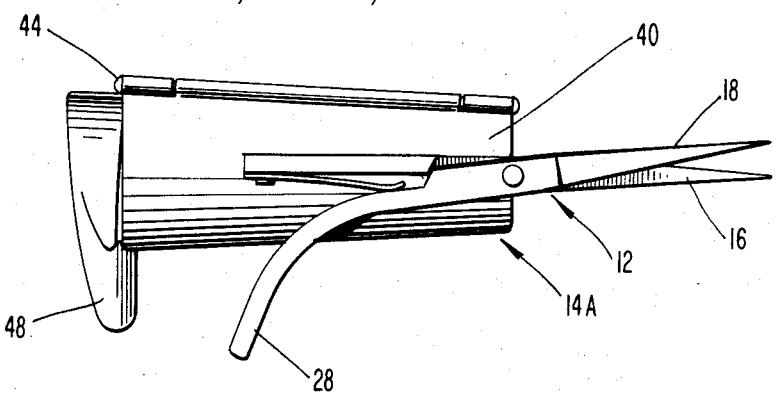
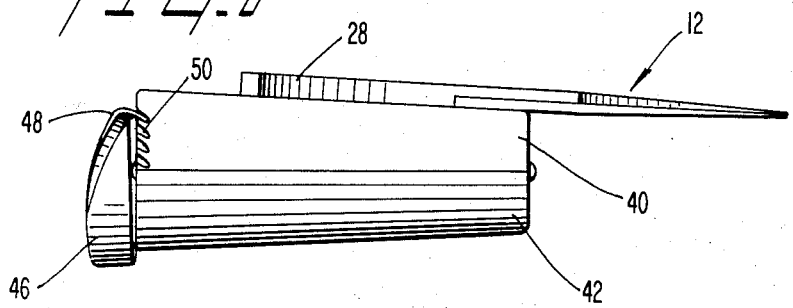
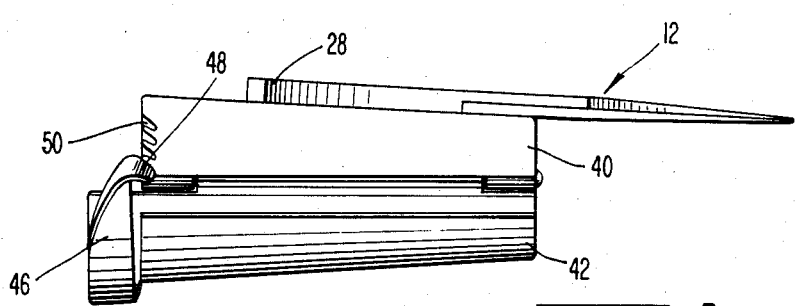
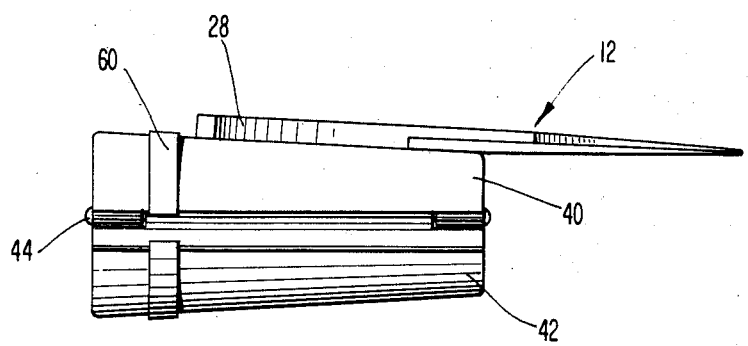

SURGICAL CUTTING INSTRUMENT

BACKGROUND AND OBJECTS OF THE INVENTION

The present invention relates to surgical instruments and, in particular, to a hand-held scissors for suture-cutting and light debridement.

Surgical activities involving the stitching of human tissue require that the suture be severed when the stitching has been completed. This may require that the surgeon release his grasp of the needle holder in order to take hold of a scissor and make the cut. Then the needle holder must be regrasped to make the next stitch.

Surgical activities may involve other manipulations, such as light debridement, which require the surgeon to release hold of one instrument in order to take hold of a scissor.

Clearly, it would be desirable in situations such as those described above if the cuttings could be made without the need to release an instrument already being held.

It is, therefore, an object of the invention to provide a cutting instrument which minimizes or obviates problems of the type described above.

Another object is to enable surgical cutting steps such as suture cutting or light debridement to be performed without requiring the release of an instrument already in a user's grasp.

A further object is to enable cutting to be performed without displacing the object being cut, to any appreciable extent.

SUMMARY OF THE INVENTION

These objects are achieved by a cutting instrument and a method of its use. The instrument is carried on a finger of a user's hand. The cutting instrument comprises a sleeve mountable on such finger, and a scissor mounted on the sleeve. The scissor includes a single cutting edge and a single movable cutting edge, each projecting forwardly of the sleeve and finger. The movable edge is mounted for rotation and includes an actuating arm extending generally laterally of the sleeve and toward the next adjacent finger of the hand so as to be moved rearwardly and displace said movable edge to a cutting position relative to the stationary blade by downward bending of the adjacent finger.

The sleeve may be made adjustable so as to fit fingers of different size.

THE DRAWINGS

The objects and advantages of the invention will become apparent from the following detailed description of preferred embodiments thereof, in connection with the accompanying drawings in which like numerals designate like elements, and in which:

FIG. 1 is a perspective view of a hand of a surgeon holding an instrument in a left-hand and carrying a cutting instrument according to the present invention on the small finger of the same hand;

FIG. 2 is a longitudinal sectional view taken through an upper portion of the cutting instrument;

FIG. 3 is a plan view of the cutting instrument, with the scissor in an open condition;

FIG. 4 is a view similar to FIG. 3 depicting the scissor in a closed cutting mode;

FIG. 5 is a plan view of a modified form of the cutting invention;

FIG. 6 is a side elevational view of the instrument depicted in FIG. 5, in one position of adjustment;

FIG. 7 is a view similar to FIG. 6, with the sleeve in another position of adjustment; and FIG. 8 is a side elevational view of an adjustable sleeve bearing a split retainer ring.

DETAILED DESCRIPTION OF PREFERRED EMBODIMENTS OF THE INVENTION

A preferred surgical cutting instrument 10 according to the present invention comprises a scissor-type cutter 12 carried by a finger mount 14. The finger mount 14 is in the form of a sleeve designed to fit over a finger, preferably, the small finger SF of a user, such as a surgeon, as depicted in FIG. 1.

The sleeve may be tapered, such that the cross-section diminishes forwardly much in the manner of a thimble, to provide a relatively secure fit on fingers of different size. The sleeve 14 can be of any suitable length sufficient to securely fit the finger and support the scissor.

The scissor 12 is preferably of the iris type and comprises a stationary blade 16 and a movable blade 18. The stationary blade 16, which is stationary in the sense of being immovable relative to the small finger SF, is suitably secured to the sleeve 14 by welding or suitable fasteners, such as rivets 20 and is arranged to project forwardly beyond the tip of the sleeve 14. Thus, the stationary blade 16 projects forwardly beyond the end of the small finger SF.

The movable blade 18, which also projects forwardly of the finger and sleeve, is pivotably mounted to the stationary blade by a pin 22 at a point intermediate the ends of both blades 16, 18 such that the pivot axis extends through the sleeve 14. A leaf spring 24 mounted to the stationary blade 16 contacts the movable blade 18 to bias the latter toward an open or non-cutting position maintaining a recess 26 between the cutting portions of the blades (FIG. 3). A stop (not shown) can be provided on the sleeve 14 or stationary blade 16 for limiting travel of the movable blade 18 away from the stationary blade (i.e., in a counterclockwise direction as viewed in FIG. 3).

The rear end of the movable blade 18 comprises an actuator arm 28 which extends generally laterally outwardly of the sleeve 14 and is tangent to an uppermost part of the sleeve 14. It will be appreciated that the sleeve 14 can be oriented such that the actuator arm can be engaged by the adjacent ring finger RF. The actuator arm 28 is preferably oriented so that by pivoting the ring finger about the mid-joint K, the ring finger engages the actuator arm 28 and urges it rearwardly, i.e., clockwise as viewed in FIG. 3 so that the movable blade 18 closes against the stationary blade 16 (FIG. 4) in the direction 30 to perform a cutting action. Thus, the actuator arm is arranged such that a rearward force F applied thereto will have a major component F1 acting perpendicular to an imaginary line 32 extending between the pivot axis 22 and the point of application of the force F. In this manner, a sufficient moment M is generated to overcome the resistance of the spring 24.

The blades 16, 18 are oriented such that the cutting recess at the mouth 26 opens forwardly. That is, the blades project forwardly, generally parallel to the small finger SF and constitute, in effect, an extension of that finger. This greatly facilitates the maneuvering of the scissor 12 and enables precise movements to be made toward the object being cut, e.g., sutures, skin tissue, etc. Preferably, the spring 24 maintains the scissor open such that the cutting recess at the mouth 26 is from ¼ to ½ inch in length and ⅛ to ¼ inch wide at the mouth so that the object to be cut (suture, tissue, etc.) can be easily received therein without being pulled, stretched or pushed to any appreciable extent.

In the case of cutting sutures, it is highly desirable to quickly position the suture within the recess and sever the suture without deflecting the suture to any appreciable extent. Such an advantage is achieved by the present invention since one of the blades 16 is stationary. By positioning the suture against the stationary blade 16 and then actuating the movable blade 18, the latter moves across the suture and severs same without any appreciable deflection of the suture occurring.

It will be appreciated that a similar advantage cannot be achieved by scissors wherein both blades move relative to the small finger.

An alternate preferred form of the instrument is depicted in FIGS. 5-7 wherein the sleeve 14A is of adjustable cross-section. The sleeve 14A comprises a pair of generally semi-cylindrical sections 40, 42 which are hinged about an axle 44 extending generally parallel to the sleeve axis. Thus, the sections 40, 42 can be rotated relative to one another about the hinge axis to increase or decrease the cross-sectional size of the sleeve and adapt the sleeve to the size of the surgeon's finger. Means are provided for retaining the sections in their adjusted position. For example, the inner end of one of the sections 42 can have an integral strip 46, the tip 48 of which is selectively engageable in a series of notches 50 formed in the inner end of the other section 40. Thus, the strip 46 may engage different ones of the notches to hold the sections in a closer condition (FIG. 6) or a separated condition (FIG. 7).

Preferably, the sections 40, 42 are not perfectly semi-cylindrical, but are rather tapering so as to have a larger inner opening (i.e., the opening at the left in FIGS. 5-7).

The stationary and movable blades 16, 18 of the scissor 12 are mounted on the top of the section 40 by a weld or adhesive.

In another preferred embodiment depicted in FIG. 8, the hinged sleeve sections 40, 42 are yieldably urged together by means of a split ring 60, in lieu of employing a strip 46. Thus, the sleeve expands to conform to the size of the finger when the instrument is inserted onto the finger.

To utilize the instrument 10 during a surgical operation, the instrument 10 is placed preferably upon the small finger SF during certain stages of the surgery, or possibly during the entire surgical operation. During periods of non-use, the instrument can be turned such that the actuator arm 28 extends up or down, i.e., does not impair use of the ring finger RF. When needed, the instrument can be rotated by engagement of the actuator arm 28 into its actuating position wherein it extends toward the ring finger, as depicted in FIG. 1. FIG. 1 depicts the surgeon's left-hand as grasping a conventional needle holder clamp 70 which is typically employed during suturing. The clamp 70 can be gripped by the thumb and either the forefinger as shown, or by another finger or the palm. After a needle (not shown has been pulled through the skin by the needle holder 70 and a stitch has been completed, the needle is held by the surgeon's right-hand (not shown) to orient the suture in a taut condition for cutting. Instead of the surgeon having to release the needle holder 70 and pick-up a scissor with the left, hand, however, it is merely necessary to extend the small finger SF toward the suture until the suture enters the recess mouth 26 and rests against the stationary blade 16, whereupon actuation of the movable blade 18 by the ring finger RF causes the suture to be cut. This action can be effected without deflecting the suture to any appreciable extent since (i) maneuvering of the scissor is simplified by virtue of its extending well forwardly of the sleeve 14 and small finger SF and (ii) the suture can rest against a stationary blade while being cut.

It will be understood that the scissor 12, while depicted in FIG. 1 as being mounted atop the sleeve 14 can, in the alternative, be mounted on the underside of the sleeve. Note that the instrument according to the present invention can be removed from the small finger of one hand and, after being inverted, can be placed on the small finger of the other hand, with the actuating arm 28 extending toward the ring finger of such other hand.

The present invention has major utility during surgical activities, but can also be used during other cutting operations to which the present advantages pertain.

Although the present invention has been described in connection with preferred embodiments thereof, it will be appreciated by those skilled in the art that additions, modifications, substitutions, and deletions not specifically described, may be made without departing from the spirit and scope of the invention as defined in the appended claims.

What is claimed is:

1. A cutting instrument which is carried on a finger of a user's hand, said cutting instrument comprising:
   a sleeve adapted to be mounted on said finger,
   a scissor mounted on said sleeve and including:
      a single stationary cutting edge projecting forwardly of said sleeve and finger, and
      a single movable cutting edge projecting forwardly of said sleeve and finger, said movable edge being mounted for rotation about a pivot axis which extends through said sleeve and including an acutating arm extending generallly laterally of said sleeve and toward the next adjacent finger of the user's hand so as to be moved rearwardly and displace said movable edge to a cutting position relative to said stationary edge by downward bending of said adjacent finger.

2. An instrument according to claim 1 including a spring yieldably urging said movable edge open to form with said stationary edge a forwardly opening recess which is from ¼ to ½ inch long and ⅛ to ¼ inch wide at its mouth.

3. An instrument according to claim 1, wherein said sleeve is tapered such that its cross-sectional area diminishes forwardly.

4. An instrument according to claim 1, wherein said movable edge is mounted atop said stationary edge.

5. An instrument according to claim 1, wherein said sleeve is of adjustable size and includes means for holding the sleeve in various positions of adjustment.

6. An instrument according to claim 5, wherein said sleeve comprises first and second sections hinged about an axis extending generally parallel to the axis of the sleeve.

7. An instrument according to claim 6, wherein said holding means comprises a member on one section which engages respective notches on the other section.

8. An instrument according to claim 6, wherein said holding means comprises a yieldable retaining ring surrounding said sections.

9. A surgical instrument comprising:
a sleeve securable to a surgeon's small finger,
a scissor attached to said sleeve and including:
  a stationary blade mounted on said sleeve and including a cutting portion projecting forwardly beyond said sleeve and finger parallel to the sleeve axis,
  a pivotable blade pivoted to said stationary blade for rotation about a pivot axis extending through said sleeve and including a cutting portion projecting forwardly beyond said sleeve and finger and movable across said stationary cutting blade when said movable blade is pivoted in a cutting direction, and an acutation portion connected to said movable cutting portion and extending laterally of the sleeve axis and toward the next adjacent finger of the hand a distance sufficient to be engaged and pulled rearwardly by such next adjacent finger to move said movable cutting portion in a cutting direction, and
spring means for urging said cutting portions apart to define a single forwardly open cutting recess therebetween of at least ¼ inch in length and ⅛ inch in width at its mouth.

10. A method of cutting with a cutting instrument in one hand comprising the steps of:
carrying on a finger of said hand a sleeve from which a scissor projects forwardly parallel to the sleeve axis and includes a single stationary edge and a single movable edge spring-urged apart to define a single forwardly open cutting recess disposed forwardly of said finger,
extending said finger toward an object to be cut to receive said object in said recess and resting against said stationary edge, and
downwardly bending the adjacent finger into engagement with a lateral actuator arm attached to said movable edge to move said arm rearwardly and displace said movable edge into cutting engagement with said stationary edge to cut the object.

11. A method according to claim 10, wherein said downwardly bending step is performed while holding another instrument in said hand.

12. A method according to claim 11, wherein said cutting is performed during a surgical operation.

13. A method according to claim 10 including the step of continually biasing said recess open such that its length is maintained at least at ¼ inch and its width at a mouth thereof is maintained at least at ⅛ inch.

* * * * *